United States Patent [19]
Landgraf et al.

[11] Patent Number: 4,460,337
[45] Date of Patent: Jul. 17, 1984

[54] DENTAL HANDPIECE

[75] Inventors: Hermann Landgraf; Werner Schuss, both of Heppenheim; Rainer Worschischek, Lorsch, all of Fed. Rep. of Germany

[73] Assignee: Siemens Aktiengesellschaft, Berlin & Munich, Fed. Rep. of Germany

[21] Appl. No.: 408,125

[22] Filed: Aug. 13, 1982

[30] Foreign Application Priority Data

Aug. 20, 1981 [DE] Fed. Rep. of Germany ....... 3132995

[51] Int. Cl.³ .............................................. A61C 1/00
[52] U.S. Cl. .................................................... 433/29
[58] Field of Search .......................... 350/96.2; 433/29

[56] References Cited

U.S. PATENT DOCUMENTS

| 3,109,238 | 11/1963 | Marks | 433/29 |
| 3,590,232 | 6/1971 | Sadowski | 433/29 |
| 4,020,556 | 5/1977 | Sotman | 433/29 |

FOREIGN PATENT DOCUMENTS 6940204 3/1971 Fed. Rep. of Germany ........ 433/29

Primary Examiner—Robert Peshock
Attorney, Agent, or Firm—Hill, Van Santen, Steadman & Simpson

[57] ABSTRACT

The present invention is directed to a dental handpiece having two parts which are coupled together for relative rotation on the axis of the dental handpiece characterized by an arrangement for conveying light through the handpiece and including a rotatable optical coupling having at least one transmission ring.

29 Claims, 22 Drawing Figures

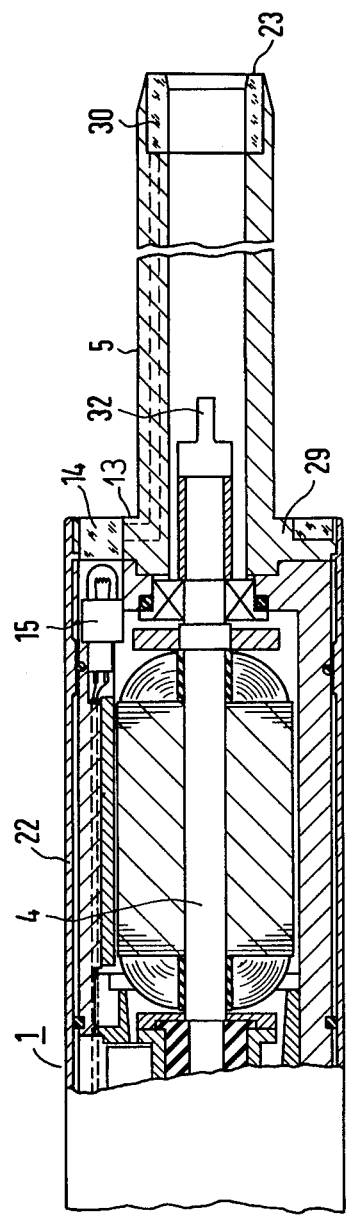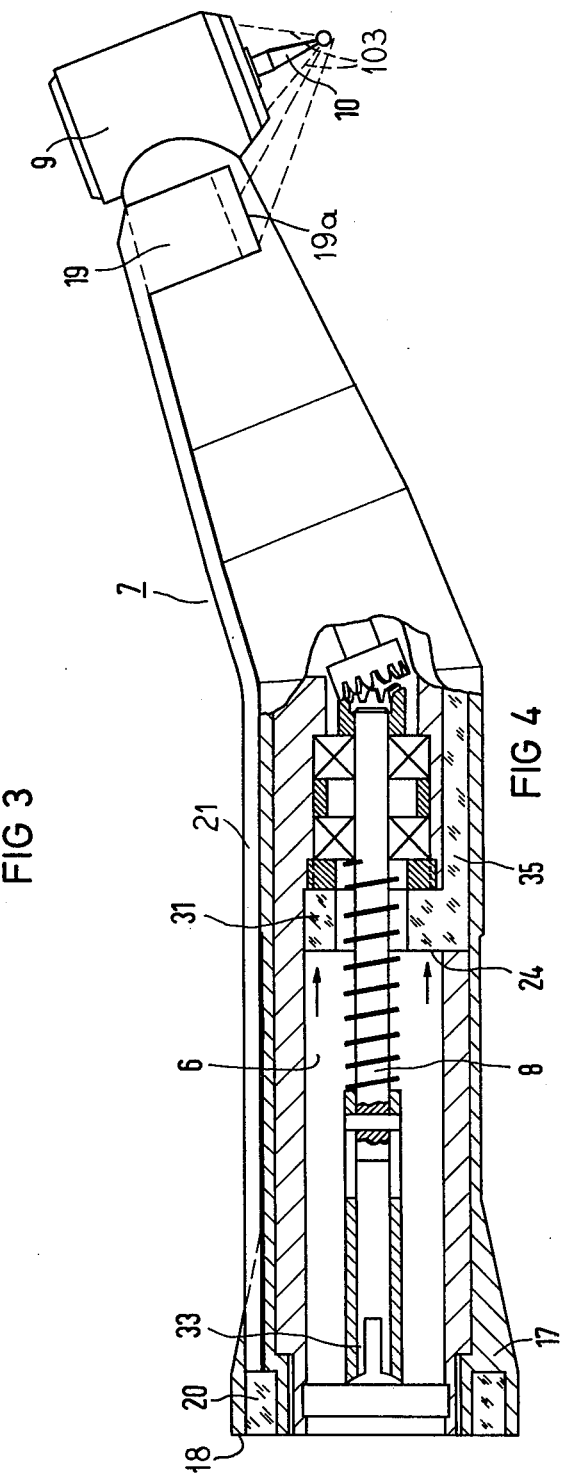

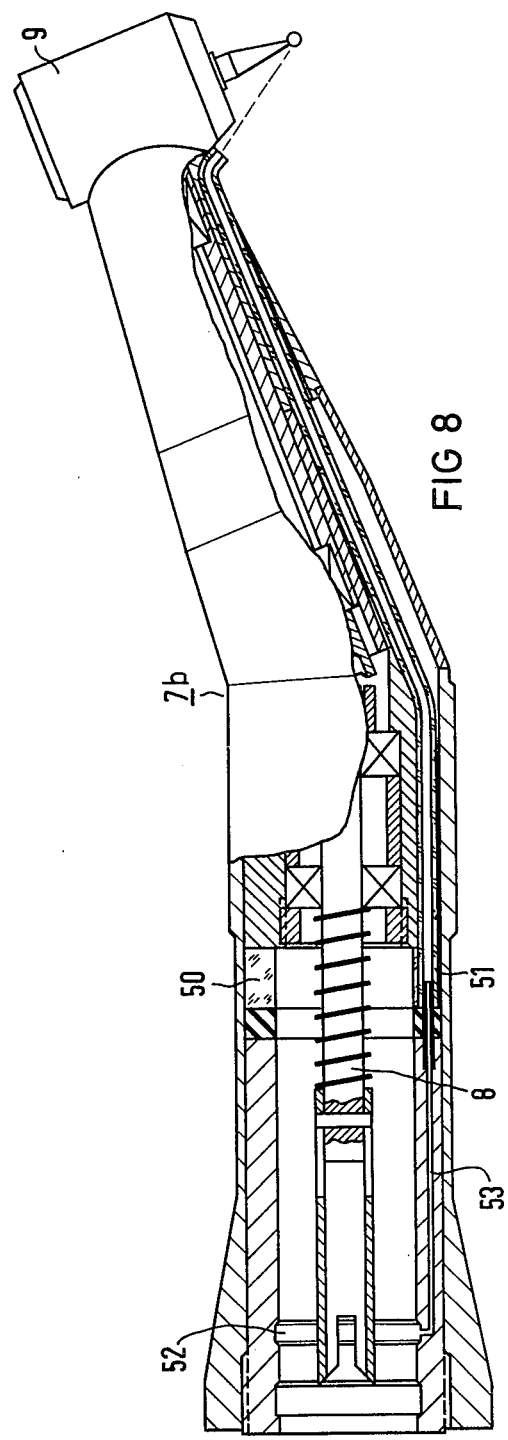
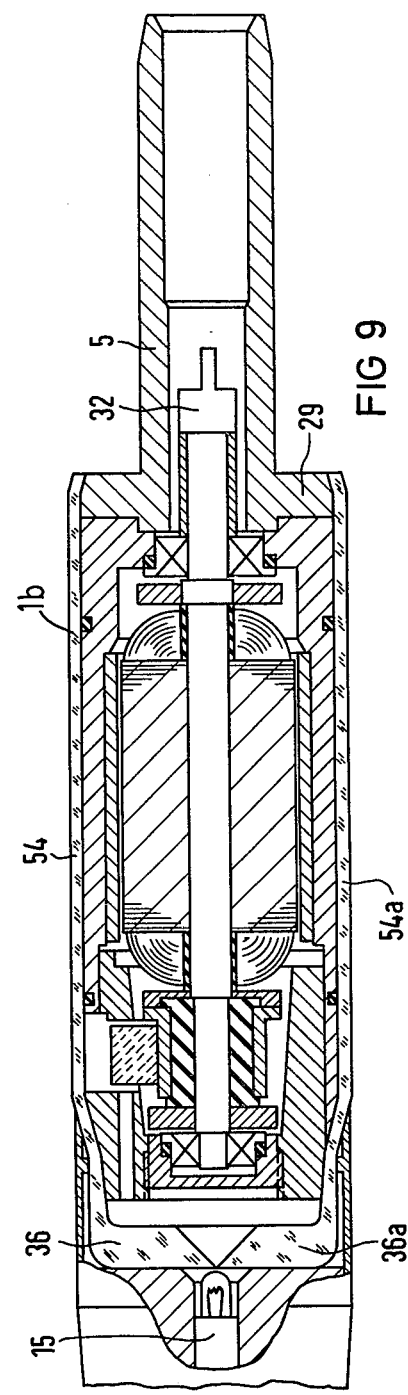
FIG 8
FIG 9

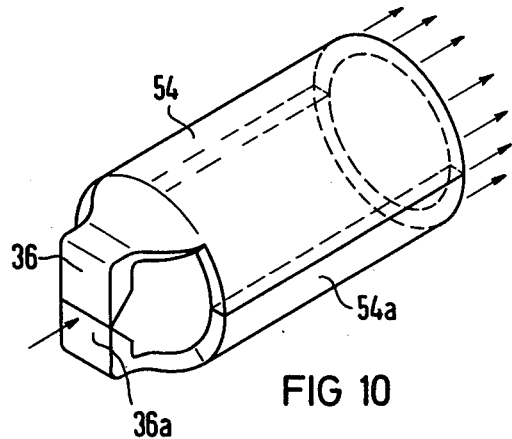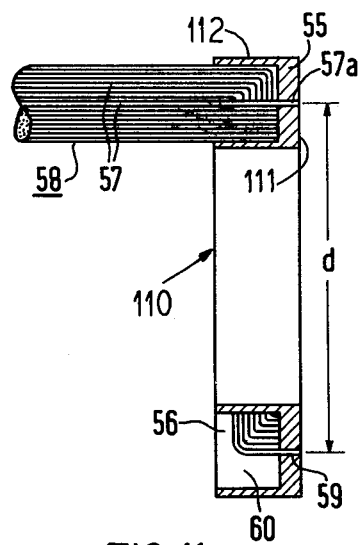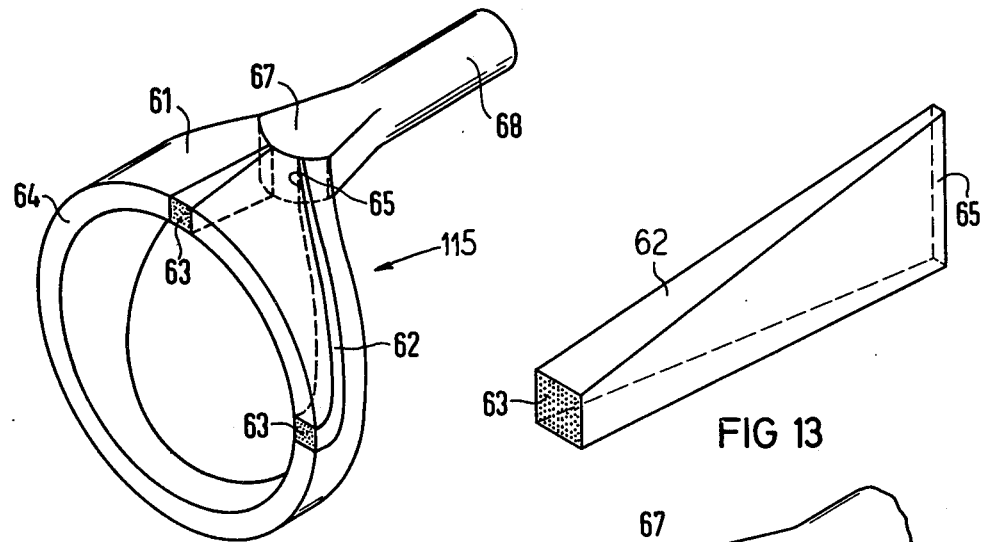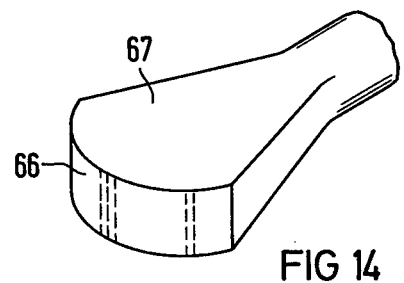
FIG 10
FIG 11
FIG 12
FIG 13
FIG 14

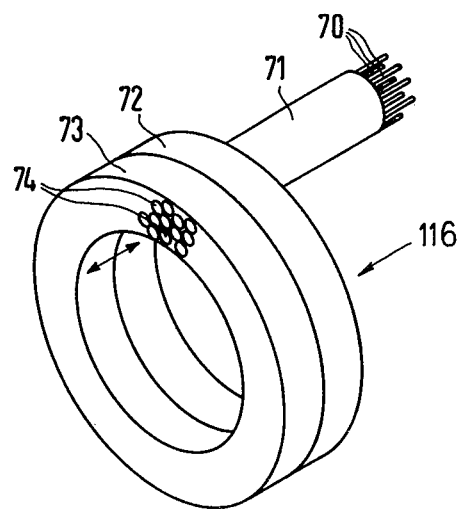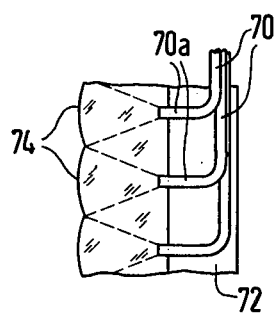
FIG 15
FIG 16
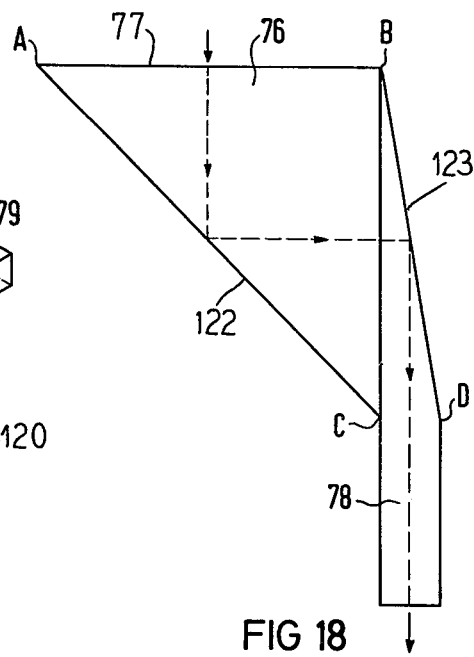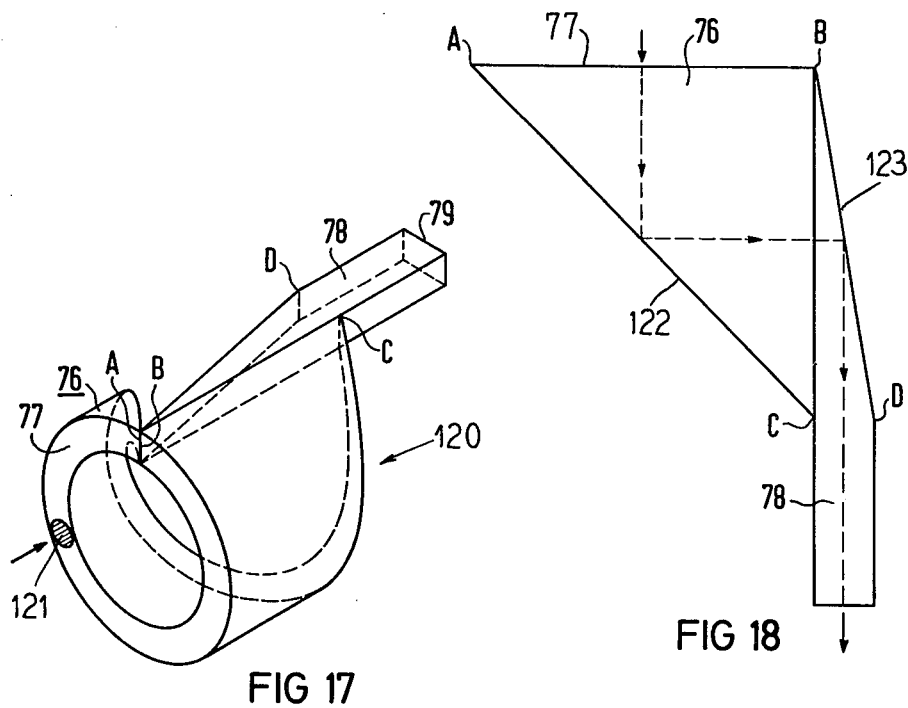
FIG 17
FIG 18

4,460,337

DENTAL HANDPIECE

BACKGROUND OF THE INVENTION

The present invention is directed to a dental handpiece having a first and second handpiece parts which are coupled together by guide elements to allow relative rotation on a longitudinal axis of the handpiece and has a light conductor arrangement for conducting light to adjacent a head housing on one of the parts of the handpiece.

It is known to provide a dental handpiece, which has two part detachably coupled together by a coupling arrangement which allows relative rotation of the parts on the longitudinal axis of the handpiece and which handpiece has a light conductor that is clipped to the outside of the handpiece for conveying light to the head portion of the handpiece from a light source. An example of such an arrangement is disclosed in German Gebrauchsmuster No. 69 40 204. In this reference, the light conductor is guided in a hollow channel of a multichannel hose, which in order to guarantee the rotatability of the two handpiece part is clipped at the head of the handpiece and also connected to the handpiece adjacent to supply hose with an excess length so that the multichannel hose is loosely positioned on the handpiece. Such a loose disposition of the light conductor and hose is disruptive and has a very negative influence on the manipulation of the handpiece parts. Also, it does not guarantee an unlimited rotation of the handpiece parts.

SUMMARY OF THE INVENTION

The present invention is directed to providing a dental handpiece which avoids disruptive cables and is an improvement in comparison to handpiece with cables. The dental handpiece of the present invention makes it possible to conduct light from one dental handpiece to the other dental handpiece part for the illumination of a treatment location, for example, the patient's mouth with the lowest possible light losses and without interfering with the rotatability of the two parts.

These objects are accomplished by an improvement in dental handpiece which has first and second handpiece parts, coupling means for detachably coupling the first and second parts together for relative rotation on a longitudinal axis of the handpiece and including a guide element at the end of each part. These guide elements comprise a projecting sleeve or peg on an end of one of the two parts and a corresponding socket formed by a sleeve on the other part. The coupling means will also include latch means for holding the parts in the coupled relationship and enabling relative rotation there between. The first part will have a head housing at an end opposite the guide element and the handpiece has means for providing light to the head. The improvements comprise the means for providing light including said first part having a light conducting element extending from adjacent the head housing to a point adjacent to the guide element of the part, the second part having a light conducting element coupled to a source of light and extending to a point adjacent to the guide element of the second part and optical means for forming a rotatable optical coupling between said conducting elements including a light transmission ring and a transfer element, said ring being coaxially positioned on one of said parts and coupled to the conducting element and said transfer element being disposed on the other part and coupled to the conducting element so that when the parts are coupled together the transfer element optically engages the ring to transfer light there between.

In some of the embodiments, the light transfer element is also a light transmission ring aligned coaxially with the light ring and transfer element may be constructed to transfer light in a direction extending radially to the axis of the handpiece or in a direction extending parallel to the axis of the handpiece. The source of light may be disposed in a remote position from the handpiece with the light being conducted along a supply hose or cable to the handpiece or the source may be a lamp disposed in the second handpiece part and connected to the conducting element.

If the second part contains a drive motor, the light conducting element may be curved members, which extend between the various magnetic shells of the motor or on the outer surface of the motor housing. If the second part has a transmission ring and has a guidance element comprising a projecting sleeve which is connected by a flange to the housing of the second part, the ring may be disposed in the area of the flange portion or may be on the projecting sleeve or peg. The transfer element may be a ring element, which is disposed in a socket like guide element to engage the ring element on the sleeve or which is positioned either on the end of the first handpiece part or in an adaptor applied to the first handpiece part to engage the ring on the flange of the guide element of the second part.

Transmission ring and the transfer element may have various structures. For example, the ring may have a member holding a one or more coaxial, circular rows of fibers. The ring can be formed by a multitude of light waveguide elements, which are arranged with one end forming an annular ring and the other end connected to a collecting prism. The ring can also consist of a multitude of individual optical fibers whose ends are disposed uniformly around a circumference of an annular carrier and are in optical contact with convergent lenses mounted on the carrier. Another form of the ring has a right triangle which has been formed so that one of the base edges forms an annular ringlike surface and the hypotenuse forms a curved deflection surface and the right triangle is utilized in conjunction with a collection prism which is connected to the other edge.

Finally, the light transmission ring and transfer element can comprise a pair of annular channel parts having reflective surfaces positioned to form a closed annular channel when the two parts are connected. The transfer element is a prism like element extending into the close channel to obtain light reflected therein. In one embodiment, the second prism element is used for introducing light into the annular channel.

A BRIEF DESCRIPTION OF THE DRAWINGS

FIG. 3 is an enlarged side view of the drive part with portions broken away for purposes of illustration of the handpiece of FIG. 1;

FIG. 4 is an enlarged side view of the grip sleeve with portions broken away for purposes of illustration of the handpiece of FIG. 1;

FIG. 8 is an enlarged side view with portions broken away for purposes of illustration of a grip part utilized with a driven part of FIG. 5;

FIG. 9 is a side view with portions broken away for purposes of illustration of yet another embodiment of the drive part of the present invention;

FIG. 10 is a perspective view of the light conducting element of the embodiment of FIG. 9;

FIG. 11 is a cross sectional view of an embodiment of a light transmission ring in accordance with the present invention;

FIG. 12 is a perspective view of another embodiment of a light transmission ring in accordance with present invention;

FIG. 13 is a perspective view of one of the elements utilized for forming the ring of FIG. 12;

FIG. 14 is a perspective view of the collecting prism which is utilized to form the ring illustrated in FIG. 12;

FIG. 15 is a perspective view of a still further embodiment of a light transmission ring in accordance with present invention;

FIG. 16 is a partial cross sectional view of the ring of FIG. 15;

FIG. 17 is a perspective view of a still further embodiment of light transmission ring in accordance with the present invention;

FIG. 18 is a development view of a portion of the ring of FIG. 17.

DESCRIPTION OF THE PREFERRED EMBODIMENTS

Figure 1:
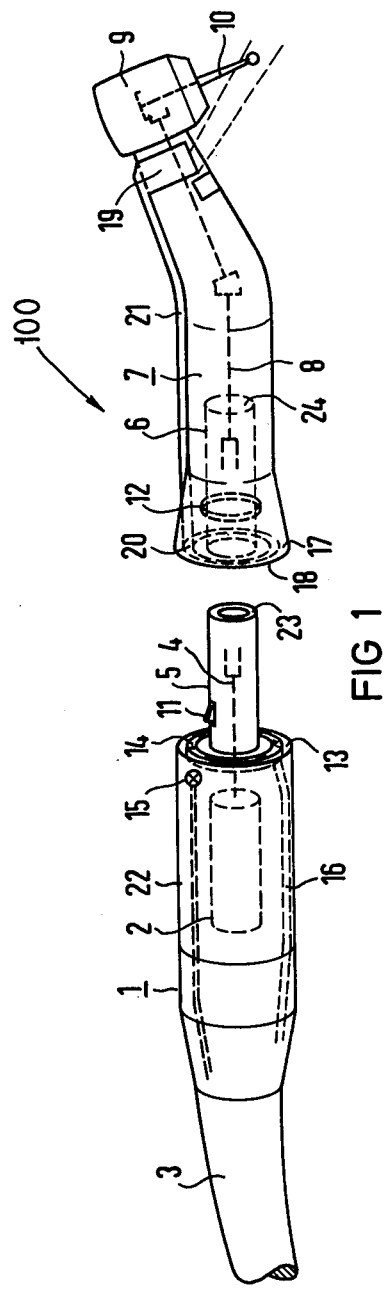
FIG. 1 is a side view of a dental handpiece in accordance with the present invention.
Figure 2:
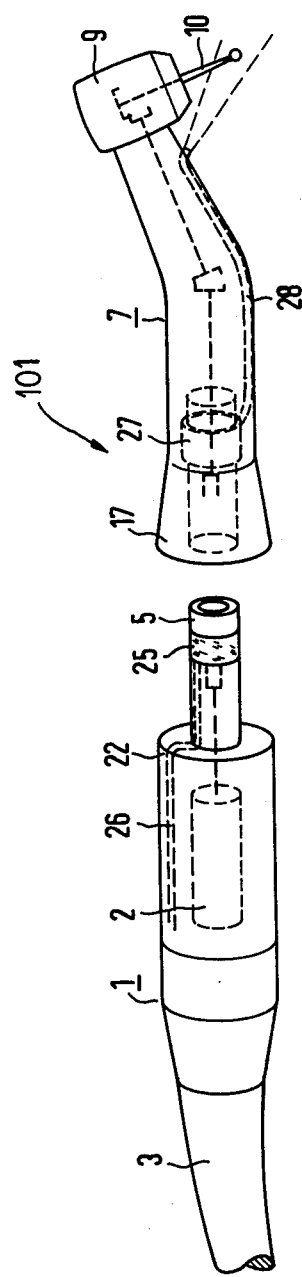
FIG. 2 is a side view of an embodiment of a dental handpiece in accordance with the present invention.

Principals of the present invention are particularly useful in a dental handpiece generally indicated at 100 in FIG. 1 or in an embodiment of the handpiece generally indicated at 101 in FIG. 2.

The dental handpiece 100 has a dental drive part 1 which is schematically illustrated as having an electric motor 2 with a drive shaft 4 which motor receives electrical energy in a known manner from a supply hose 3. The drive part or second part 1 on an end opposite the hose 3 has a guide element, which is illustrated as a guidance sleeve or peg 5 that surrounds the drive shaft 4 of the motor 2. A first handpiece part or gripping part 7 has a guide element in the form of a socket or sleeve 6, which telescopically receives the sleeve 5 to form coupling means which coupled its two parts 1 and 7 together for rotation around the longitudinal axis of the handpiece 100. While in the coupled position, the drive shaft 4 is coupled to a drive shaft section 8, which through a series of drive shafts sections drives a socket which rotatably supports a tool 10 in a head housing 9 of part 7.

The coupling means includes a known catch nose or detent 11, which is resiliently urged outward from the sleeve 5 and is engaged in the corresponding annular groove 12 in the socket formed by the guide element 6. The detent 11 and the groove 12 forms the latch means which hold the two parts 1 and 7 in the coupled position and prevents unintentional disengagement of the two parts while allowing relative rotation therebetween. It should be noted that the latch means is expediently designed in such a manner that the gripping part 7 is easily separated from the drive part 1 without the assistance of any tools.

Drive part 1, as illustrated in FIG. 1, has an end surface or shoulder 13 which is formed by a flange 29 (FIG. 3) of the guide element 5. The shoulder 13 has an annular light transmission ring 14 which is connected directly either to a lamp 15 or to a light conductor 16, which is connected in turn to a light source through appropriate light conducting elements in the hose 3. The gripping part 7 has a conical adaptor 17 (best illustrated in FIG. 4) which matches the smaller outside diameter of the gripping part 7 to the larger diameter of the drive part 1. As illustrated in FIGS. 1 and 4, the adaptor 17 has an endface 18 which supports a transfer element which is illustrated as a second light transmission ring 20. The light transmission ring 20 is the same size as the light transmission ring 14 and when the parts 1 and 7 are coupled together, the light transmission ring 20 will engage the ring 14 so that light can be conducted therebetween. In the device 100, the ring 20 is connected by a light conductor 21, which extends along the outside of the grip part 7, to a clip 19 which clip forms a light exit location 19a for directing light, as shown in broken lines, on the tool 10.

In the above described embodiment, the light transmission occurs through two light transmission rings disposed coaxially relative to the guidance sleeve or peg 5. The light transmission rings are disposed on the end surface 13 of a motor housing 22 of the drive part 1 and also an end surface 18 of the adaptor 17. Instead of utilizing ring 14 on end surface 13 and a ring 20 on a surface 18, the part 1 can be provided with a transfer element or ring which is positioned on an end surface 23 of the sleeve 5 to be coaxial with a transmission ring or transfer element in the part 7 which is at a position 24 which is adjacent the end of the socket or sleeve 6. This structure will be discussed in later detail.

In the embodiment of the dental handpiece generally indicated at 101 in FIG. 2, a light transmission ring 25, which has a radial light emission surface, is provided on the circumference of a guidance peg or sleeve 5 of the second or drive part 1. The transmission ring 25 is coupled to light conductor 26 which again extends along the sleeve 5 and the housing 22 to a light source which may be in the drive part 1 or removed from the dental handpiece and connected by appropriate light conductors in the supply hose 3. The grip part 7 has a light transmission ring 27, which is concentrically arranged relative to the light transmission ring 25 when the two handpiece parts are coupled together. As illustrated, the ring 27 forms a portion of the surface of the socket like guide element 6 and is optically coupled to the light conductor 28 which extends in the part 7 to adjacent the head housing 9 to project light on the tool 10.

An advantage of utilizing the adaptor 17 having a ring 20 that forms an optical coupling with the ring 14 of the handpiece 100 of FIG. 1 over the radial transfer of light formed by the rings 25 and 26 in the devise 101 is that the conical shaped adaptor is an existing part of the handpiece arrangement. Thus the replacement with a part having the transfer ring does not require any additional space in the grip sleeve or part 7.

FIGS. 3 and 4 are enlarged views of the handpiece parts 1 and 7 of FIG. 1 with the latch means that is formed by the detent 11 and groove 12 being omitted. As illustrated in FIG. 3, the light source is a filament lamp 15, which is positioned directly adjacent the transmission ring 14, which has a portion acting as a light conductor connecting the ring 14 to the lamp 15. As shown in greater detail, the motor shaft 4 has a dog 32, which is received in a coupling slot 33 of the drive shaft section 8 (FIG. 4). The housing 22, which receives the drive motor 2 is connected to the flange 29 of the guidance element 5 and this flange 29 supports the light transmission ring 14. It should be noted, that the electrical supply lines for the lamp 15 extend in hollow channel in the motor to the supply hose and are not described in greater detail.

As mentioned hereinabove, the device 100 of FIG. 1 could have an alternate arrangement with a transmission ring 30 being positioned at the end of the element 5 and having a light emitting surface 23, which is coupled to an endface 24 in a socket formed by the guidance element 6 of the part 7. As illustrated in FIGS. 3 and 4, the transmission ring 30 is provided in a counter bore in the hollow sleeve of the guidance element 5. The face or surface 24 is a portion of a transmission ring 31 which is coupled to a light conductor 35 which extends towards the head housing 9 and is provided with an outlet, which will be discussed hereinafter, for projecting light 103 on the tool 10.

Figure 6:
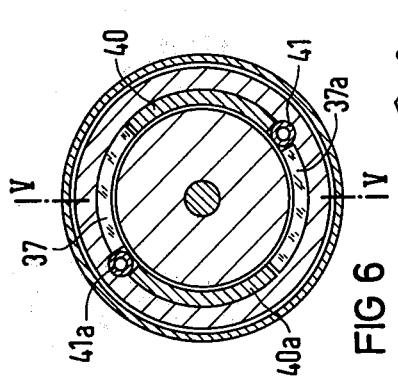
FIG. 6 is a transverse cross sectional view of the drive part of FIG. 5.
Figure 5:
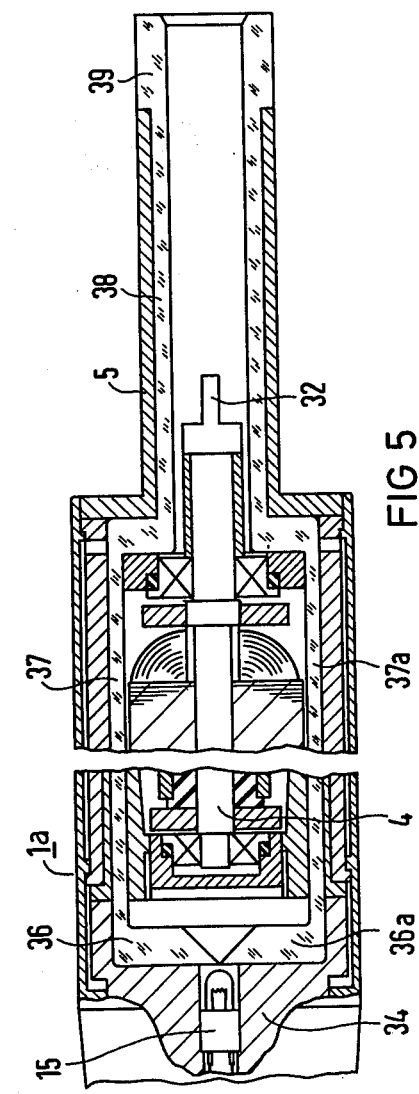
FIG. 5 is a cross-sectional view with portions in elevations taken on line V—V of FIG. 6 of an embodiment of a drive part in accordance with the present invention.

In FIG. 5, an embodiment of the second or drive part 1a is illustrated. In this embodiment, the lamp 15 is disposed in a connection part 34 of the drive part. To convey light from the source used by the bulb 15, the housing of the drive part 1a has a pair of curved plate conducting elements 37 and 37a which are best illustrated in FIG. 6. The conducting element 37 and 37a adjacent one end have end pieces 36 and 36a respectively which extend radially inwardly and terminate adjacent to bulb 15. The end pieces 36 and 36a are provided with mirrored surfaces which extend at a 45° angle to the axis of the drive motor so that light from the bulb 15 will be reflected into the pieces 36, 36a and be transferred into the light conducting elements or bodies 37, 37a. From the elements 37, 37a, the light is transferred to light elements such as 38 in the guide element 5 to terminate in a transfer or transmission ring 39 at the end of the guide element 5. It should be noted that transfer ring 39 is constructed to emit light radially outward therefrom. As mentioned hereinabove, each of the conducting elements 37, 37a are curved plate members, which are positioned between two magnets or magnetic shells 40 and 40a and the stator of the electric motor 4. Channels or conduits 41 and 41a extend between the magnetic shells 40 and 40a and the elements 37 and 37a and serve in a conventional manner for conveying cooling fluids such as water or spray. Since the course of these types of cooling channels is well known, they are not discussed in greater detail.

Figure 7:
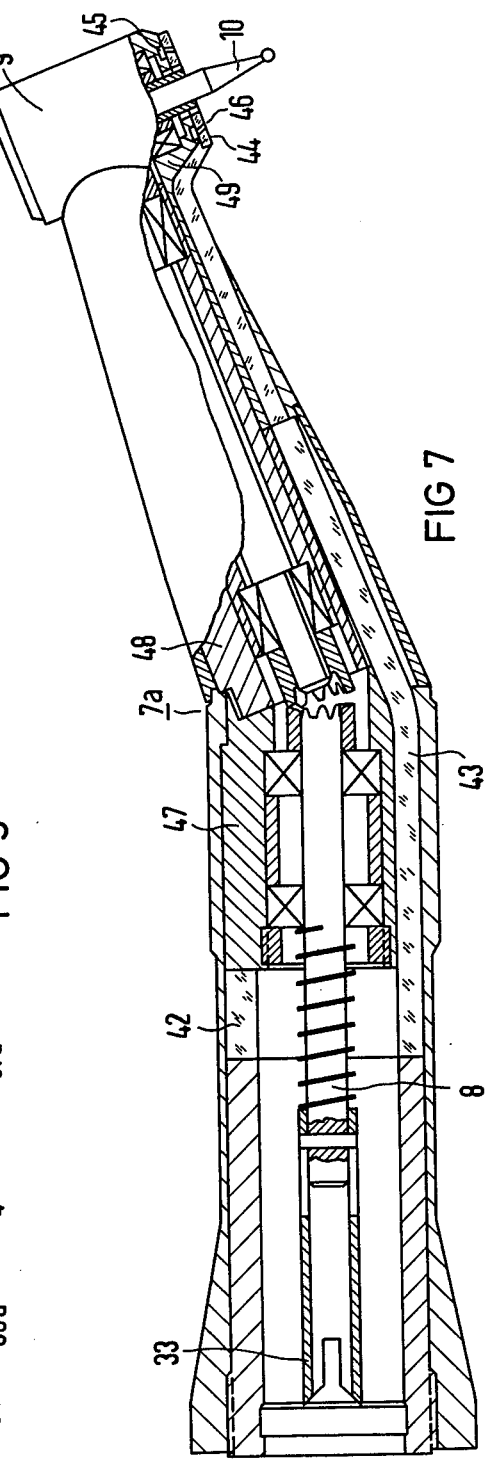
FIG. 7 is an enlarged side view with portions broken away of a grip portion utilized with the drive part of FIG. 5.
Figure 19:
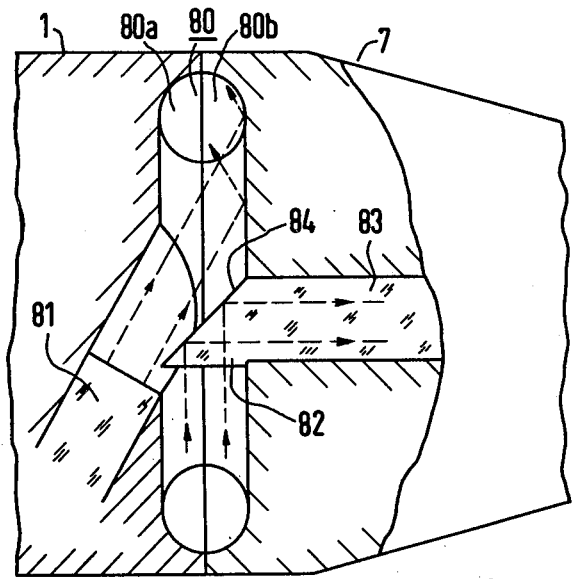
FIG. 19 is a schematic illustration of an embodiment of the transmission ring formed by reflective channels.

When utilizing a drive part having the structure of part 1a, a grip sleeve having a structure of first part 7a of FIG. 7 is utilized. The grip sleeve 7a has a light transmission ring 42 which is positioned in the socket forming the guide elements to telescopically receive te light transmission ring 39 when the two parts are assembled or coupled together. The light transmission 42 is optically coupled to light conductor 43, which has a round cross section and discharges into a cover 44 which is provided on an endface of the head housing 9 which faces the tool 10. The cover 44 forms the outer termination of a spray channel 45 and the cover consists of a light conducting material and contains one or more, discharge openings 46 for discharging the cooling fluid from the spray channel 45.

Instead of the light conduction being over individual light conductors which are separately disposed in the grip part, the grip part itself can have structured parts which are used as for light conduction. It is conceivable for example to transfer the light from the light transmission ring 42 into one of the parts 47 and through part 48 to part 49 which are formed of a light conducting material. Thus, light coupled from the ring 42 into the sleeve 47 is coupled into the sleeve 48 to be conducted into sleeve 49 for discharge in the area of tool 10.

Another embodiment of the grip piece or first part is shown by the part 7b of FIG. 8. This part 7b has a light transmission ring 50, which is similar to the ring 42 and is positioned in the socket of the guidance element of the part 7b to receive light radiations from the transmission ring 39 of the drive part 1a. The transmission ring 50 is optically coupled to a glass tube 51, which extends through the body of the grip part 7b and terminates adjacent the head housing 9. The glass tube 51 besides conveying light from the ring 50 to illuminate the tool also receives a coolant from a coolant line 53 that extends to an annular channel 52 and is connected to a coolant port in the drive part 1a in a conventional manner.

In FIG. 9 another embodiment of the drive part or second part 1b is illustrated. The part 1b deviates from the part 1a of FIG. 5 in that instead of the two end pieces 36 and 36a being connected to curve plate light conductors 37 and 37a that extend through the magnetic shells of the drive motor, they are connected to semi-cylindrical members or semi-monocoques 54 and 54a which surround the outer jacket of the drive motor and terminate at the end of the flange 29 of the guide element 5. As illustrated in FIG. 10, the two semi-cylindrical members 54 and 54a form an annular ring, which can cooperate with the transfer element in the grip sleeve or part. It should be noted that the transfer of light can be in a direction parallel to the axis of the part such as indicated by the arrows in FIG. 10 or it can be a radial transmission to a sleeve like transmission element provided on the first or gripping part.

Although each of the described embodiments utilizes a pair of light transmission rings as means for forming an optical connection or coupling, it is conceivable that one of the rings be replaced by a transmission or transfer element so that only one light transmission ring is provided on one of the two handpiece parts and the other transfer element is provided on the other part. For example, the transfer element can be one or more optical conductors extending from one or more sources of light in the part 1 and the transmission ring is disposed on the grip sleeve. Instead of a ring in the grip part or sleeve 7, one or more transfer elements, such as light conductors can be used to engage the ring of the part 1.

In the following FIGS. 11–16, different embodiments of light transmission rings are illustrated for transfering the light in a direction extending substantially parallel to the axis of the handpiece. However, with minor modifications, each of the rings can be constructed to transfer the light radially in a manner similar to the transmission rings illustrated in FIGS. 5 and 7.

An embodiment of the transmission ring is generally indicated at 110 in FIG. 11 and is constructed for transmitting the light in an axial direction between two handpiece parts. The ring 110 can be utilized for the positions 14,20,30 and 31 as illustrated in FIGS. 3 and 4. The light transmission ring 110 is formed by carrier part 55, which has an annular recess or cavity 56 in which the individual fiber optical waveguides 57 of a fiber optical bundle 58 are laid or positioned. The fibers are positioned with each fiber extending through an aperture or bore 59 so that the fiber end 57a of each fiber are uniformly distributed along a circle of diameter d. This can be accomplished by providing a plurality of bores 59 in the carrier part 55 on the desired circle having the diameter d. The fibers in a cavity or recess 56 have their ends positioned or extending through their respective apertures 59 and then the remaining portions 60 of the cavity is filled with a suitable filling compound for example a casting resin so that the individual fibers are fixed in the carrier part 55. In order to obtain a planer endface, the endface of the carrier part and fibers after the mounting of the fibers is then polished.

As a result of the arrangement, a light flux from optical fiber waveguides has a circular cross section and thus a point of punctiform emission to a diameter which is significantly greater in contrast thereto is possible and vice versa. In order to improve the light intensity, a plurality of these circularly disposed optically fiber waveguides can be concentrically arranged one about another on the carrier part. In other words, instead of this single circle of ends 57, concentric circles are provided.

It is also conceivable and within the framework of the invention to have the optical fibers terminate not on the end face 111 of the carrier part 55 but to terminate on a circumferential surface 112. Thus a radial light transfer similar to the rings 25 and 27 in FIG. 2 or rings 39 and 47 FIGS. 5 and 7 is possible. It should be noted, that if the fibers are arranged to provide a radial like transfer, a series of radial circles of fiber ends on the surface 112 can be utilized.

Another embodiment of a light transfer ring is generally indicated at 115 in FIG. 12. The ring 115 is composed of a plurality of individual fiber optical waveguides 62 which have end 63 and 65. The waveguides 62 are distributed on the circumference of an annular carrier part 61 in such a manner that the ends 63 terminate and form an end face with an annular surface 64 and completely fills up this annular cross section. The other ends 65 (FIG. 13) are optically coupled to a surface 66 of a collecting prism 67 (FIG. 14). To retain the end surfaces 63 and 65, the individual fiber optical waveguide 62 are designed approximately wedge shape. A fiber optical waveguides 68 with the circular cross section is connected to the collecting prism 67. The collecting prism 67 as well as the individual waveguides 62 are advantageously manufactured of optical glass but can also be formed of individual optical fibers.

In FIGS. 15 and 16, another embodiment of a light transmission ring is generally indicated at 116. Here the individual waveguides 70 of an optical waveguide bundle 71 are uniformly mounted in the circular or ring carrier 72 in a manner similar to the ring 110 of FIG. 11. A ring 73 with a multitude of convergent optical lenses 74 is placed and located on the end face of carrier 72. The optical lenses 74 form light transmission surfaces and concentrate the incident light into the optical ends 70a of the waveguide 70 which ends are located in the focus of the lenses as illustrated in FIG. 16. As in the sample embodiments described above, the sum of the waveguide 70 disposed on a circumference of the carrier part 72 correspond to a plurality of fiber optical waveguides contained in the fiber bundle 71. The convergent lenses 74 are advantageously disposed in such a manner so that the space occurring between the individual fiber optical waveguides 70a are fully filled out.

Another embodiment of light transmission ring is generally indicated at 120 in FIG. 17 and is particularly suitable for receiving a punctiform of light such as illustrated by the spot 121 which spot can be created by a single light conductor or element. Such a light transmission ring 120 thus is to be provided when only one handpiece part is provided with a light transmission ring and the other handpiece part in contrast thereto only has a punctiform transmission of the light to enable full rotatability of the two handpiece parts. Here the light transmission ring 120 consists of a deflection prism 76, which exhibits a circular light entry surface 77 and is optically coupled to a collection prism 78 whose free end 79 forms a waveguide for conducting the light that is connected into the ring 120. In a developed view of FIG. 18, the deflection prism 76 has the form of a right triangle with corners A, B and C. The end face or edge that extends between the corners A and B forms a light entry surface. A surface 122 extending along the hypotenuse between the corners A and C and a surface 124 between the corners B and C are mirrored and therefore leads to the required deflection of light according to the illustrated arrows, whereby the surface 124 has a one-side permeable layer, *permitting the light to enter from prism 76 into prism 78 but preventing the light to go back to the prism 76. The diagonal surface 123 between corner B and corner D of the collecting prisms 78 is selected in such a manner that the light is forwarded approximately in the direction of the waveguide coupled to the end 79. In order to obtain the optimum light guidance, the remaining surfaces of the two elements 76 and 78 which are preferably glass elements are provided with mirrored outer layers surfaces.

As mentioned herein above, the ring 120 is particularly useful for punctiform light incident on the end surface 77 of the glass member 76. However, it can also be utilized for a circular light coupling.

Figure 20:
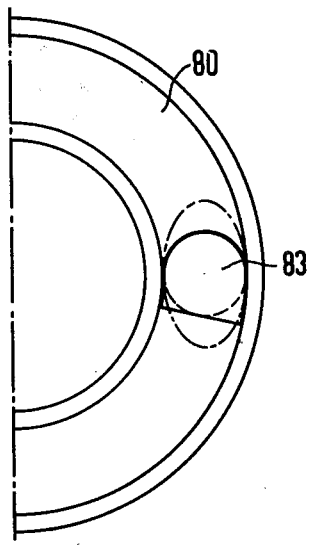
FIG. 20 is an end view of a portion of the channel of FIG. 19.

The embodiments illustrated in FIGS. 19 through 22 can only be utilized when a light transmission ring is provided in both handpiece parts. Thus, for example, in the previously described arrangement these rings 25 and 27 of FIG. 2, 39 and 42 of FIGS. 5 and 7 or 39 and 50 in FIGS. 5 and 8. In the embodiments of FIGS. 19 through 22, the light transmission ring in both handpiece parts 1 and 7 consists of channel halves 80a and 80b which coact together to form a ring channel 80. The ring channel 80 is either mirrored or polished to a very high polish on its inside surface walls and as a result the light fed in through a waveguide such as 81 is reflected by the wall surfaces as illustrated by the arrows in FIG. 19. The outer handpiece part 7 is provided with a special waveguide 83 which has an end piece 82 that extends into the channel 80. The end piece 80 forms a deflection prism and has a surface 84 which slants at 45° to the axis of waveguide 83 and is provided with a mirror so that light received from the ring channel 80, as illustrated by the arrows, is reflected parallel to the axis of the waveguide 83. Since, as shown by FIG. 20, the optical waveguide 83 is disposed outside the longitudinal axis at symmetry of the handpiece part, the rotatability of the two handpiece part up to 360° is possible.

Figure 21:
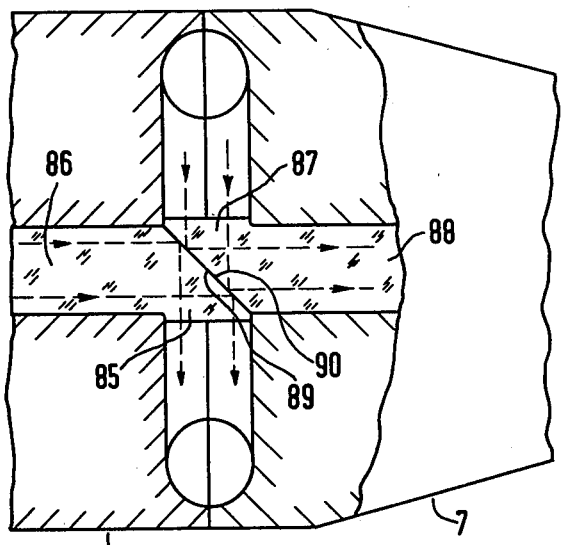
FIG. 21 is an embodiment of the transmission ring of FIG. 19.
Figure 22:
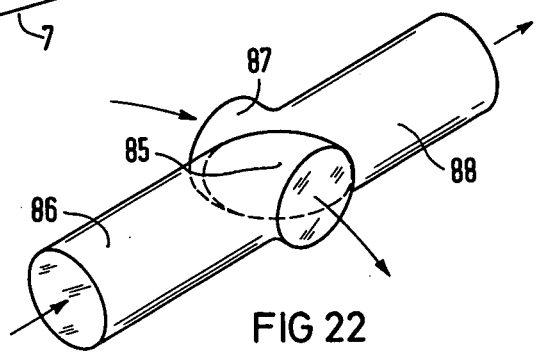
FIG. 22 is a perspective view of the two prism elements utilized with the embodiment of FIG. 21.

In an embodiment illustrated FIG. 21, the light that is introduced into the channel 80 is introduced from an end 85 of an optical waveguide 86. The end 85 as well as the end 87 of the waveguide 88 in the other part have a prism like shape with two surfaces 89 and 90 extending at 45° to the axis of the respective waveguide. These surfaces 89 and 90 are optically insulated from one another so that no light diffraction can occur at the two optical ends. As in the previous embodiment, the waveguides 85 and 87 are also positioned offset from the longitudinal axis of symmetry of the handpiece part and as a result the light transmission will occur for any rotary position at the handpiece parts. However, it should be noted that the amount of rotation of the two parts relative to each other will be limited due to the ends 85 and 87 extending into the channel 80.

Even though the coupling locations in the illustrated sample embodiments is always the rotational location of the two handpiece parts as well, this is nonetheless, not absolutely necessary. Rotational and parting locations thus can also be separately disposed at different locations of the handpiece part. The light transmission ring or light transmission rings are then to be disposed at the rotational locational. A light transmission at the parting location, what has no rotation, can then accomplish by means of light waveguide ends with a flush engagement with each other.

Although various minor modifications may be suggested by those first in the art, it should be understood that we wish to embody within the scope of the patent granted hereon all such modifications reasonably and properly come within the scope for our contribution to the art.

We claim:

1. In a dental handpiece having first and second handpiece parts, coupling means for detachably coupling the parts together for relative rotation on a longitudinal axis of the hand piece, said coupling means including a guide element at one end of each part and latch means for holding said parts in a coupled relationship and enabling relative rotation therebetween, said first part having a head housing at an end opposite to the one end for supporting a tool, said first and second parts having means for transferring drive energy from the second part through the guide elements to the head housing of the first part to drive the tool, and said hand piece having means for providing light to the head housing, the improvements comprising said means for providing light including a light source mounted in the second part, a light conducting element in each of said first and second parts and optical means for forming a rotatable optical coupling between the conducting element of the first part and the conducting element of the second part, said coupling means including a transfer element and a light transmission ring having an annular light receiving surface, said light transmission ring being coaxially mounted on the longitudinal axis of the first part adjacent the guide element and being coupled to the light conducting element of the first part extending to a point adjacent the head housing, and said transfer element being coupled to the light source by the conducting element of the second part and being positioned adjacent the guide element of the second part so that when the two parts are coupled together, the transfer element optically engages the receiving surface of the ring to transfer light from the source to the ring for all positions of relative rotation between the parts.

2. In a dental handpiece according to claim 1, wherein said second part contains a drive motor with a drive shaft, said guide element of the second part being a tubular sleeve having a flange connecting the guide element to a motor housing with the sleeve surrounding said drive shaft, and said transfer element is a light transmission ring disposed on said flange.

3. In a dental handpiece according to claim 1, wheren said transfer element is a light transmission ring so that both parts have light transmission rings.

4. In a dental handpiece according to claim 1, wherein the light transmission ring and the transfer element are disposed on end surfaces of the handpiece parts.

5. In a dental handpiece according to claim 1, wherein the light transmission ring is disposed on a circumferential surface of the handpiece part and the transfer element is readily positioned to said ring so that the light during coupling extends radially to the handpiece axis.

6. In a dental handpiece according to claim 1, wherein the parts have different outside diameters with the first part having the smallest outside diameter being provided with an adaptor, said transmission ring being disposed in said adaptor.

7. In a dental handpiece according to claim 2, wherein the light source is disposed immediately adjacent to the transmission ring of the second part.

8. In dental handpiece according to claim 1, when the second part contains an electric drive motor with permanent magnetic shells and a drive shaft, said guide element of said second part being a guidance sleeve having a flange connecting said element to a motor housing with the drive shaft in said sleeve, the light source being a filament bulb positioned at an end of the second part opposite to said drive shaft, said light conducting elements being curved plate elements extending between said magnetic shells and having first ends extending radially inward to the light source with opposite ends terminating adjacent said guide element.

9. In a dental handpiece according to claim 8, wherein said transfer element is a second transmission ring, the end faces of each of the first end of the conducting elements are provided with reflecting means and said conducting elements being connected to said second transmission ring disposed on the sleeve of the guide element.

10. In a dental handpiece according to claim 1, wherein the second part contains an electrical drive motor having a drive shaft, said guide element being a sleeve member with a flange secured to a motor housing with the sleeve member surrounding the shaft, said light conducting elements being semicylindrical sleeve members having an end surface disposed adjacent to said light source with said sleeve member being disposed on the outer surface of said motor housing and terminating in a transfer ring on said flange to form the transfer element.

11. In a dental handpiece according to claim 1, wherein the guide element of the first part comprises a socket like member for receiving a tubular guide element of the second part, said light transmission ring being disposed on an inside surface of said socket part.

12. In a dental handpiece according to claim 11, wherein the light conductor extending to the head housing terminates in an annular element on an end face of the housing facing the tool.

13. In a dental handpiece according to claim 11, wherein the light conducting element of the first part comprises a tubular element of light conducting material connected to a source of coolant for discharge on the tool.

14. In a dental handpiece according to claim 12, wherein the annular element forms a cover of a fluid ring channel and has at least one fluid discharge opening.

15. In a dental handpiece according to claim 11, wherein the first part is composed of at least one transparent light conducting structural member, said transparent light conducting structural member forming said light conducting element.

16. In a dental handpiece according to claim 15, wherein at least two of the members forming the first handpiece part are of light transmitting material one of said members forming and end face of the head housing facing the tool and being optically connected to at least one other member forming the light conducting elements.

17. In a dental handpiece according to claim 1, wherein the light transmission ring comprises a carrier supporting a multitude of optical fiber waveguide ends uniformly distributed with their end faces on at least one circle.

18. In a dental handpiece according to claim 17, wherein said carrier comprises an annular ring containing an annular recess in communication with a plurality of apertures, said fibers are being disposed in said annular recess with the ends extending through respecting apertures and being held by a filling material disposed in said annular recess.

19. In a dental handpiece according to claim 18, wherein the end faces of said fibers are arranged in at least two concentric circles of different diameters.

20. In a dental handpiece according to claim 31, wherein the light transmission ring is formed by an annular carrier supporting a plurality of light waveguide elements disposed thereon, said waveguide elements being arranged with one end face of each of said waveguide elements forming an annular surface and the other end face being coupled to a collecting prism, said conducting prism being connected to an optical waveguide.

21. In a dental handpiece according to claim 20, wherein the individual waveguide element and the collecting prism consist of optical glass.

22. In a dental handpiece according to claim 1, wherein the light transmission ring consists of an annular carrier positioning the ends of a plurality of fibers in an uniform distribution on at least one circle, said carrier positioning a convergent lens for each of end face of the fibers with the end face being disposed on the focal point of said lens, said lenses forming the light transmission surface of said ring.

23. In a dental handpiece according to claim 22, wherein the lenses are embedded in an optical carrier material.

24. In a dental handpiece according to claim 1, wherein the light transmission ring comprises a collecting prism and a glass body forming a deflection prism with one surface of the prism forming an annular surface and having the other surface forming a connection to said collection prism.

25. In a dental handpiece according to claim 24, wherein the deflection prism consists of an element in a developed view forming a right triangle with the hypotenuse forming a reflecting surface, one of the other sides forming the annular surface and the other side being optically connected to a wedge shaped portion of the collecting prism.

26. In a dental handpiece according to claim 1, wherein the light transfer element and the light transmission ring are each one half of a tubular ring channel concentrically arranged between said parts, said ring channel having a light reflective surface, said second part having the coupling element formed by a waveguide having an end provided with an oblique surface for reflecting light from the channel into said waveguide.

27. In a dental handpiece according to claim 26, wherein said waveguide of the first part extends parallel to the axis of the handpiece and the oblique surface extends at 45° to said axis, and wherein the coupling element of the second part comprises an optical waveguide discharging into the annular channel at an angle in a range of 45°-60° degrees to the longitudinal axis.

28. In a dental handpiece according to claim 26, wherein the coupling element of the second part comprises a waveguide extending parallel to the axis of the handpiece and terminating in a oblique surface for discharging light into the annular channel, said surfaces of the ends of the waveguides forming deflection prisms and being optically separated from one another.

29. In a dental handpiece having first and second handpiece parts, coupling means for detachably coupling the parts together for relative rotation on a longitudinal axis of the handpiece, said coupling means including a guide element at one end of each part and latch means for holding said parts in a coupled relationship and enabling relative rotation therebetween, said first part having a head housing at an end opposite to the one end for supporting a tool, said first and second parts having means for transferring drive energy from the second part through the guide elements to the head housing of the first part to drive the tool, and said handpiece having means for providing light to the head housing, the improvements comprising said means for providing light including a light source mounted in the second part, a light conducting element in said first part and optical means for forming a rotatable optical coupling between the conducting element of the first part and the light source of the second part, said coupling means including a light transmission ring having an annular light receiving surface, said light transmission ring being coaxially mounted on the longitudinal axis of the first part adjacent the guide element and being coupled to the light conducting element of the first part extending to a point adjacent the head housing, and said light source being positioned adjacent the guide element of the second part so that when the two parts are coupled together, light from the source is projected onto the receiving surface of the ring to transfer light from the source to the ring for all positions of relative rotation between the parts.

* * * * *